United States Patent
Zhang et al.

(10) Patent No.: US 8,137,290 B2
(45) Date of Patent: Mar. 20, 2012

(54) DEVICE AND METHOD FOR PROVIDING INFORMATION BASED ON BODY FLUIDS RELATED MATTER

(75) Inventors: Ting Zhang, Kobe (JP); Chunhua Huang, Beijing (CN); Jie Yin, Beijing (CN); Koichi Tomi, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 2023 days.

(21) Appl. No.: 10/402,665

(22) Filed: Mar. 28, 2003

(65) Prior Publication Data
US 2004/0128153 A1    Jul. 1, 2004

Related U.S. Application Data

(63) Continuation of application No. PCT/US00/29764, filed on Oct. 27, 2000.

(51) Int. Cl.
*A61B 5/00* (2006.01)
*B65D 81/00* (2006.01)

(52) U.S. Cl. ... 600/574; 604/358; 604/361; 604/385.17; 604/904; 434/367; 434/428; 434/429

(58) Field of Classification Search .......... 600/573–575, 600/584; 434/428–430, 367; 604/358, 361, 604/385.17, 385.18, 904
See application file for complete search history.

(56) References Cited

U.S. PATENT DOCUMENTS

| | | | | |
|---|---|---|---|---|
| 3,815,601 A | * | 6/1974 | Schaefer | 604/15 |
| 3,976,075 A | * | 8/1976 | Chinai et al. | 604/365 |
| 4,239,043 A | * | 12/1980 | Gellert | 604/15 |
| 4,305,391 A | * | 12/1981 | Jackson | 604/366 |
| 4,627,849 A | * | 12/1986 | Walton et al. | 604/379 |
| 5,520,203 A | | 5/1996 | Segerstrom | |
| 5,546,943 A | * | 8/1996 | Gould | 600/425 |
| 5,839,585 A | | 11/1998 | Miller | |
| 5,865,322 A | | 2/1999 | Miller | |
| 5,947,302 A | | 9/1999 | Miller | |
| 6,093,027 A | * | 7/2000 | Unger et al. | 434/429 |
| 6,183,456 B1 | * | 2/2001 | Brown et al. | 604/385.01 |
| 6,258,075 B1 | * | 7/2001 | Taylor et al. | 604/385.18 |
| 6,368,113 B1 | | 4/2002 | Unger et al. | |

FOREIGN PATENT DOCUMENTS

| | | |
|---|---|---|
| EP | 0 370 808 A1 | 5/1990 |
| JP | 05192301 A | 8/1993 |
| JP | 09051877 A | 2/1997 |
| WO | WO 97/45088 A1 | 12/1997 |

* cited by examiner

*Primary Examiner* — Rena Towa
(74) *Attorney, Agent, or Firm* — Amanda T. Barry; David M. Weirich; Kevin C. Johnson

(57) ABSTRACT

The present invention is directed to a device (or an apparatus) and a method for providing information about body fluids. The device is for measuring a body fluid discharged from a body of a user by putting a first disposable absorbent article having a predetermined absorbent capacity to a fluid discharging portion of the user. The device comprises means for inputting an amount of the body fluid which is absorbed by the first absorbent article through observation; and means for calculating the total amount of the body fluid which was discharged by the user based on the input and the predetermined absorbent capacity of the first absorbent article.

10 Claims, 2 Drawing Sheets

DEVICE AND METHOD FOR PROVIDING INFORMATION BASED ON BODY FLUIDS RELATED MATTER

CROSS REFERENCE TO RELATED REFERENCES

This is a continuation of International Application PCT/US00/29764 with an International filing date of Oct. 27, 2000.

FIELD

The present invention generally relates to information provider devices and methods, and particularly to a device and method for providing information about body fluids related matter. Examples of such information to be provided include information about amount of body fluids discharged from the human body, information about level change of discharged body fluids in a period, information about time to change a disposable absorbent article which is in use, and information about recommendable disposable absorbent articles.

BACKGROUND

Disposable absorbent articles such as sanitary napkins, pantiliners, diapers, and incontinence pads are devices that are typically worn in the crotch region of an undergarment. Interlabial devices are disposable absorbent articles that are typically designed to be worn within the interlabial space of a female wearer. Other disposable absorbent articles such as tampons are designed to be worn within the vaginal cavity. These devices are designed to absorb or otherwise contain body fluids discharged from the human body and to prevent body and clothing soiling.

It is also known that the amount of body fluids discharged from the human body is very personal, i.e., it varies depending on the person, the body condition of the person, and/or the age of the person. To protect users of disposable absorbent articles from soiling, it is known that appropriate usage of absorbent articles is necessary. For example, if a user continues to use a same absorbent article for a too long time, a leakage of absorbed body fluids may occur to soil the wearer's body and/or clothing. In another example, if a user uses a disposable absorbent article for a too short time, the absorbent article may be wasted as it has not fully absorbed body fluids yet. This sometimes causes a significant discomfort to the wearer while removing the article. These issues are more serious to tampon users who have less experience of usage and are not used to use tampons appropriately.

To address these problems, it is generally expected that a user chooses an appropriate absorbent article which is most suitable for the user, among a lot of products which are on the market, and manage the usage of the absorbent article appropriately by themselves, i.e., managing the usage time length to prevent the problems. However, there is no tool or means in the art to help the users' situation other than depending on their experience.

Based on the foregoing, there is a need for a device and method that can help the users' situation by providing information about body fluids related matter.

SUMMARY

The present invention is directed to a device (or an apparatus) for providing information about body fluids related matter. In one aspect of the invention, the device is for measuring a body fluid discharged from a body of a user by putting a first disposable absorbent article having a predetermined absorbent capacity to a fluid discharging portion of the user. The device comprises means for inputting an amount of the body fluid which is absorbed by the first absorbent article through observation; and means for calculating the total amount of the body fluid which was discharged by the user based on the input and the predetermined absorbent capacity of the first absorbent article.

In another aspect of the invention, the device is for showing a flow level change of a body fluid discharged from a body of a user. The device comprises means for measuring a body fluid discharged from a body for a first predetermined time period; and means for displaying the change of the discharged body fluid level in a display for a second predetermined time period.

In an yet another aspect of the invention, the device is for recommending a disposable absorbent article to be used by a user. The device comprises means for measuring a body fluid discharged from the body of the user for a predetermined time period; and recommendation means for recommending a disposable absorbent article based on the amount of the body fluid which was measured.

In a still another aspect of the invention, the device is for advising when a disposable absorbent article which is being used by a user needs to be replaced with a new one. The device comprises means for inputting a time when the user starts using a disposable absorbent article; timer means for measuring the lapse of time when the user continues to use the absorbent article; and notification means for notifying the change timing when the absorbent article is to be replaced with a new one, in response to the timer means.

The present invention is also directed to a method for providing information about body fluid related matter. In an yet another aspect of the invention, the method is for measuring a body fluid discharged from a body of a user. The method comprises the steps of: (a) putting a disposable absorbent article having a predetermined absorbent capacity to a fluid discharging portion of the user; (b) observing an amount of the body fluid which is absorbed by the absorbent article; and (c) calculating the total amount of the body fluid which was discharged by the user based on the observation of the step (b) and the predetermined absorbent capacity of the absorbent article.

In a still another aspect of the invention, the method is for showing, in a display, a flow level change of a body fluid discharged from a body of a user. The method comprises the steps of: measuring a body fluid discharged from a body for a first predetermined time period; and displaying the change of the discharged body fluid level in the display for a second predetermined time period.

In an yet another aspect of the invention, the method is for recommending an absorbent product to be used by a user. The method comprises the steps of: measuring a body fluid discharged from the body of a user for a first predetermined time period; and recommending the user an absorbent product for a usage for a second predetermined time period, based on the body fluid measurement.

In a still another aspect of the invention, the method is for advising when a disposable absorbent article which is being used by a user needs to be replaced with a new one. The method comprises the steps of: inputting a time when the user starts using a disposable absorbent article; measuring the lapse of time when the user continues to use the absorbent article; and notifying when the absorbent article is to be replaced with a new one.

The present invention is further directed to an educational kit for educating an appropriate use of disposable absorbent articles. The educational kit comprises a disposable absorbent article; and the device of the present invention. The absorbent article and the device are packaged in a common package.

The present invention is yet further directed to a method for educating an appropriate use of a disposable absorbent article. The method comprises the steps of: distributing a disposable absorbent article; and distributing the device of the present invention.

The foregoing answers the need for a device and method for providing information about body fluids related matter.

These and other features, aspects, and advantages of the present invention will become evident to those skilled in the art from reading of the present disclosure.

BRIEF DESCRIPTION OF THE DRAWINGS

While the specification concludes with claims particularly pointing out and distinctly claiming the invention, it is believed that the invention will be better understood from the following description of preferred embodiments taken in conjunction with the accompanying drawings wherein like designations are used to designate substantially identical elements, and in which:

DETAILED DESCRIPTION

Herein, the terms "comprise", "include" and "contain" mean that other element(s) and step(s) which do not affect the end result can be added. These terms encompass the terms "consisting of" and "consisting essentially of".

Herein, the term "disposable absorbent articles" refers to articles which absorb and contain body fluids or exudates, and more specifically, refers to articles which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and preferably, to be disposed of in an environmentally compatible manner). The disposable absorbent articles include feminine hygiene articles, diapers, incontinence pads, training pants, and the like.

Herein, the term "feminine hygiene articles" refers to disposable absorbent articles used by women for catamenial protection. Such articles include tampons, sanitary napkins, interlabial products, incontinence devices, and pantiliners. The present invention is preferably applicable to devices and methods for providing information about body fluids related matter with regards to the feminine hygiene articles, it is also applicable thereto with regards to the other disposable absorbent articles.

Figure 1:
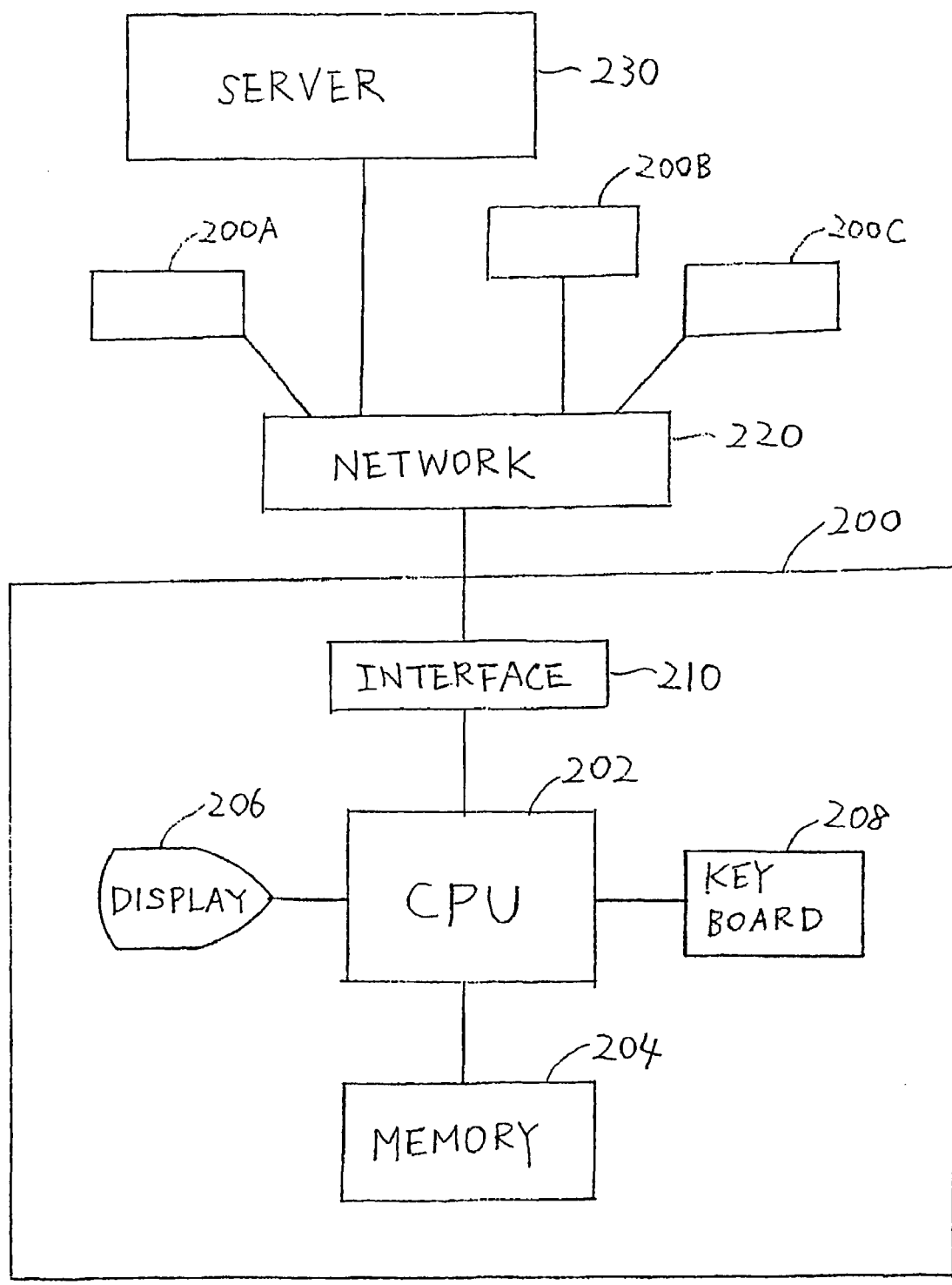
FIG. 1 is a block diagram of an information provider device which is one preferred embodiment of the present invention.

FIG. 1 is a block diagram of an information provider device 200 which is one preferred embodiment of the present invention. Referring to FIG. 1, the information provider device 200 includes a data processing means or a central processing unit (CPU) 202; a data storage means or a memory unit 204; an output means or a display unit 206; and a data or information input means or a key board 208. A user of the information provider device 200 inputs necessary data or information through the key board 208. As is described in detail hereinafter, the CPU 202 performs necessary data processing with respects to the input data in accordance with a program(s) which is stored in the memory unit 204. The resulting data is also stored in the memory unit 204, and if desired, is shown to the user through the display unit 206.

The information provider device 200 of the invention can be implemented by either a stand-alone computer or device which is not connected to any communication or computer network system. A preferred information provider device which is implemented by a stand-alone computer is available from Hong Kong Landgain Electronics Co., Ltd., Hong Kong, China.

In one embodiment wherein the information provider device 200 is implemented by a network system wherein a server computer and client computers are connected to the information provider device 200 through a network, the information provider device 200 further includes an interface unit 210 which is connected to a server computer 230 through a network 220. Herein, the term "network" encompasses both a communication network and a computer network. Herein, the term "computer network" refers to a network which includes at least two, and preferably a number of computers or devices connected through a communication line or a communication network. The communication line or network can be either wired or wireless. Preferred examples of the networks include a Local Area Network (LAN), the Internet, and variations on the Internet such as a Wireless Access Protocol (WAP) network, a mobile phone network (e.g., i-mode®) and the like. In this embodiment, the input data by a user can be sent, through the computer network 220, to the server computer 230 which performs necessary data processing of the present invention with respects to the data or information inputted by users in accordance with a program(s) which is stored in the server computer 230. The resulting data is stored in the server computer 230, and is also sent to the device 200 through the computer network 220 to display the same in the display unit 206. Other information provider devices 200A, 200B and 200C which are used by other users can be connected to the server computer 230 through the computer network 220 so that the server computer 230 can provide the same service for the other users.

In a preferred embodiment, the information provider device 200 of the present invention can measure or calculate any body fluids which are discharged by a body. Such body fluids include menstruation fluids such as menses, urine, feces, blood, saliba and the like. Depending on the target body fluids to be measured or calculated, the fluid discharging portion in the body changes. In preferred embodiments, the fluid discharging portion is in the crotch region. For example, if the body fluid is menses and the disposable absorbent article is a tampon, the fluid discharging portion is the vaginal cavity of a female wherein the tampon is worn or inserted within the vaginal cavity for absorption of menstrual flow therefrom. In another example, if the body fluid is urine or feces and the disposable absorbent article is a diaper, the fluid discharging portion is the crotch region.

To measure or calculate body fluids discharged, a disposable absorbent article (i.e., a first disposable absorbent article) which has a predetermined absorbent capacity is put to a fluid discharging portion of a body of a user. Any disposable absorbent articles known in the art which have a predetermined absorbent capacity can be used. Herein, the term "predetermined absorbent capacity" is intended to mean a preliminarily known amount of body fluids which can be absorbed by the absorbent article and can be used for the calculation for the discharged body fluids herein. Any number which is within the maximum absorbent capacity of the absorbent article can be used as long as such number can provide an estimated amount of body fluids discharged through the calculation herein. A preferred predetermined absorbent capacity is the average absorbent capacity of the disposable absorbent article.

Although any disposable absorbent article known in the art can be used as the first disposable absorbent article, a tampon, an interlabial product, or a sanitary napkin is preferably used as the first disposable absorbent article. In the following, preferred embodiments wherein a tampon is used as the first disposable absorbent article are described in detail for the sake of simplicity of description. Thus, in those embodiments the fluid discharging portion of a body is the vaginal cavity of a female user. Herein, the term "vaginal cavity" is intended to refer to the space located between the introitus of the vagina (sometimes referred to as the sphincter of the vagina) and the cervix and is not intended to include the interlabial space, including the floor of vestibule. The externally visible genitalia generally is not included within the term "vaginal cavity".

The tampons or tampon products herein referred to may be any suitable conventional catamenial tampons which are on the market, including any of the tampons sold under the trademark "TAMPAX" and distributed by The Procter & Gamble Company of Cincinnati, Ohio (USA). The tampons used with regards to the preferred embodiments herein may be either of the applicator insertion type or digital insertion type, and any suitable applicator known in the art may be used (including, e.g., a cardboard applicator or a plastic applicator). In use, the tampon is inserted into the vaginal cavity of the wearer. Preferred tampon products which are already in market under the trademark "TAMPAX" include "Lites", "Regular", "Super" and "Super Plus" (and their equivalents sold with the corresponding names in other languages) which have different predetermined absorbent capacities. In a preferred embodiment, the predetermined absorbent capacities for these tampon products are within the same ranges as those determined as the ranges of absorbency in grams according to The US FDA (Food & Drug Administration), Code of Federal Regulations, Title 21, CFR 801.430. Specifically, the test method for determining the rages of absorbency is described in CFR 801.430(f)(2). For example, the "TAMPAX" tampon products "Lites", "Regular", "Super" and "Super Plus" have the ranges of absorbency of about 4-6 grams, 6-9 grams, 9-12 grams and 12-15 grams, respectively. Any numbers within respective ranges are preferably used in the calculation herein as the predetermined absorbent capacities for the respective tampon products. For example, the lowest number, the middle number or the highest number in each range can be used as the predetermined absorbent capacities for the respective tampon products. In a preferred embodiment, the lowest numbers in each range (i.e., 4 grams, 6 grams, and 9 grams) are used for the calculation.

Figure 2:
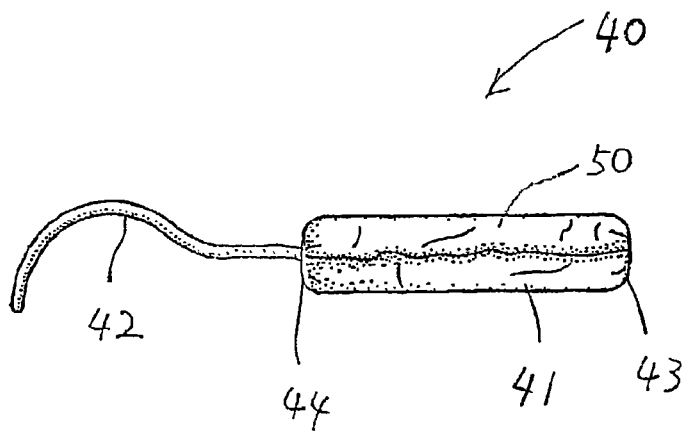
FIG. 2 is a front view of a tampon which is one preferred example of disposable absorbent articles of the present invention.

FIG. 2 is a front view of a tampon 40 which is one preferred example of disposable absorbent articles. Referring to FIG. 2, the tampon 40 includes a primary absorbent member (sometimes also referred to as the "absorbent core") 41 and a withdrawal cord 42 which is joined to the primary absorbent member 41. The primary absorbent member 41 of the tampon 40 has an insertion end 43 and a withdrawal end 44. The primary absorbent member 41 can be compressed into a generally cylindrical configuration in the radial direction, the axial direction, or in both the radial and axial directions. While the primary absorbent member 41 is preferably compressed into a substantially cylindrical configuration as shown in FIG. 2, other shapes such as rectangular, triangular, trapezoidal, and semi-circular shapes are also possible. The tampon 40 has the body facing surface 50 which is fluid permeable. The body fluids which contact the body facing surface 50 are absorbed by the primary absorbent member 41.

Preferably, the wearing time length during which the absorbent article has been put to the fluid discharging portion is measured. Alternatively, the user can be requested to put the absorbent article in a predetermined time length. A preferred time length is at least about 30 minutes, more preferably from about 1 hour to about 8 hours. In the preferred embodiment wherein a tampon is inserted into the vaginal cavity, the time length is from about 1 to about 8 hours, preferably from about 4 to about 8 hours.

After the absorbent article has absorbed body fluids discharged from the fluid discharging portion of body, the absorbent article is removed from the fluid discharging portion of the wearer or the user. The degree of the amount of the body fluids which has been absorbed by the absorbent article is then observed by the user. This observation can be done by a visual inspection by the user. Herein, the term "visual inspection" is intended to mean that the level of the amount of the body fluids which was discharged is estimated through the observation on the soiled absorbent article by the user's eyes. Through this observation, at least a rough estimation of the ratio of the soiled area versus the total area of liquid permeable material on the body facing surface (e.g., the body facing surface 50 of the primary absorbent member 41 of the tampon 40) of the absorbent article is obtained as the degree of the absorbent amount by the user's visual inspection.

In a preferred embodiment, at least two, more preferably at least three (or four) levels of the amount of the body fluids absorbed by the article are identified as the degree of the absorbent amount by the visual inspection. For example, "full absorption" and "partial absorption" are observed by more than 50% of soiled area and less than 50% of soiled area, respectively. In another example, "very full absorption", "full absorption" and "partial absorption" are observed by more than about 70% of soiled area, between about 30% and 70% of soiled area and less than about 30% of soiled area, respectively.

More preferably, the level of the amount of the body fluids absorbed by the article is observed by the user by a percentage of the soiled area versus the total area of liquid permeable material of the absorbent article.

In a preferred embodiment, the occurrence, preferably the degree of leakage is also observed, and considered in the calculation of the body fluids discharged. Herein, "leakage" is intended to mean a part of discharged body fluids which is not absorbed by the absorbent article and moves away from the absorbent article when it is worn by the user. In one preferred embodiment, the occurrence of leakage is only observed. Alternatively, at least two, more preferably at least three (or four) levels of the amount of the body fluids leaked are identified as the degree of leakage through the user's visual inspection. For example, "heavy amount", "small amount" and "none" are observed for the three levels' observation.

The information about at least the degree of the absorbed amount of the body fluids which is obtained by the visual inspection is then inputted to the device 200 by the user through the key board 208. Preferably, the information about the degree of the leakage which is obtained by the visual inspection is also inputted by the user. The input operation is preferably done by the user after the use of each absorbent article. Preferably, the input operation is done immediately after the observation is conducted on each absorbent article.

Based on the data or information inputted by the user, the information provider device 200 calculates the flow level of the body fluids HA (grams/hour) which was discharged from the body per one hour by the following mathematical expression:

$$HA = AC \times AF / WT \quad (1)$$

wherein AC (grams): the predetermined absorbent capacity of the absorbent article used;

AF: the area factor (i.e., a ratio of the soiled area versus the total area of liquid permeable material of the absorbent article); and WT (hours): the wearing time length.

In the preferred embodiment wherein the degree of leakage is considered, the amount of the body fluids HA is obtained by the following mathematical expression:

$$HA = (AC \times AF + LF) / WT \quad (2)$$

wherein LF: the leakage factor.

The leakage factor LF is an estimated amount of body fluids (grams) which was leaked from the absorbent article during the use. The degree of the leakage observed by the user is converted into the estimated amount of body fluids which is used in the expression (2) as the leakage factor LF. A preferred example of the relationship between the degree of the leakage observed and the leakage factor LF is shown in Table I.

TABLE I

| Degree of the Leakage | Leakage Factor (LF) |
|---|---|
| No Leakage | 0 |
| Some Leakage | 0.5 |
| A lot of Leakage | 1.0 |

Assuming the user uses m (m is equal to or more than 2) of disposable absorbent articles in one day and the user inputs all necessary data or information correctly, the calculation by the expression (1) or (2) is performed on each of the m absorbent articles thereby obtaining the average amount of the body fluids AHA (grams) which was discharged per one hour on each day by the following mathematical expression:

$$AHA = (\Sigma HA(j)) / m \quad (j = 1, 2, \ldots, m) \quad (3)$$

wherein HA (j): the amount of the body fluids which was discharged per one hour based on the measurement of the j-th absorbent article.

Thus, the average amount of the body fluids AHA on each day can be obtained from the mathematical expression (3). The average amount of the body fluids AHA on the k-th day (hereinafter referred to as "Day (k)") is referred to as AHA (k) hereinafter. Assuming the user has n days in the menstruation period in the current menstruation cycle, the observation (and necessary data inputs based on the observation) is carried out for the all of n days, i.e., Day (1), Day (2), ..., Day (k−1), Day (k), Day (k+1), ..., Day (n). The average amounts of the body fluids which were discharged on the respective days AHA (1), AHA (2), ..., AHA (n) are obtained from the mathematical expression (3).

If the user uses no absorbent article (or does not input necessary data) on Day (k) in the menstruation period in the current menstruation cycle but uses absorbent articles (and does input necessary data) on the other days, e.g., Day (1), Day (2), ..., Day (k−1), Day (k+1), ..., Day (n), the average amount of the body fluids AHA (k) (grams) which was discharged but is missing on Day (k) in the current menstruation cycle can be obtained by referring to some of the previous data AHA (1)', AHA (2)', ..., AHA (n)' which were already obtained from the previous menstrual cycle. Specifically, either of the following mathematical expressions can be used for obtaining the average amount of the body fluids AHA (k):

$$AHA(k) = \{AHA(k)' / AHA(k-1)'\} \times AHA(k-1) \quad (4)$$

$$AHA(k) = \{AHA(k)' / AHA(k+1)'\} \times AHA(k+1) \quad (5)$$

In the event that the current menstruation cycle is the first cycle for the user, and thus no data for the previous menstruation cycle is available, the device 200 requests the user to input an estimated flow level on each day in one typical menstruation period. Each level inputted by the user is converted into pseudo-average amounts of the body fluids AHA (1)', AHA (2)', ..., AHA (n)' which are referred by the mathematical expressions (4) or (5). A Preferred example of the relationship between the predetermined body fluids levels and the pseudo-average amounts of the body fluids is shown in Table II.

TABLE II

| Body Fluids Levels | AHA (k)' |
|---|---|
| Light Flow | 0.7 gram |
| Moderate Flow | 1 gram |
| Heavy Flow | 1.5 grams |
| Extra Heavy Flow | 2 grams |

Assuming the user uses (or consumes) M (M is equal to or more than 2) of disposable absorbent articles in one menstruation period, the maximum amount of the body fluids MHA (grams) which was discharged for one hour is obtained by the following mathematical expression:

$$MHA = \text{Maximum}\{HA(k)\} \ (k=1, 2, \ldots, M) \quad (6)$$

Wherein Maximum {x1, x2, ..., xM}: the function which chooses the maximum number among the numbers x1, x2, ..., xM.

HA (k): the body fluids which were discharged for per hour based on the calculation on the k-th absorbent article in the menstruation period.

Thus, the possible total maximum amount of the body fluids MQDA (grams) which was discharged for six hours is calculated by the following mathematical expression:

$$MQDA = MHA \times 6 \quad (7)$$

The total amount of the body fluids DA (grams) which was discharged per one day (i.e., 24 hours) can be obtained by the following mathematical expression:

$$DA = AHA \times 24 \quad (8)$$

Similarly, the total amount of the body fluids QDA (grams) which was discharged per 6 hours can be obtained by the following mathematical expression:

$$QDA = AHA \times 6 \quad (9)$$

Typically, women have from about 5 to about 8 menstruation days in one menstrual period. In a preferred embodiment, the total amount DA of the body fluids which was discharged per one day is calculated by the expression (8) for each menstruation day. Thus, the total amount TDA of the body fluids which was discharged during the whole menstruation period (which includes n menstruation days) is obtained by the following mathematical expression:

$$TDA = \Sigma DA(k) \ (k=1, 2, \ldots, n) \quad (10)$$

wherein DA(k): the total amount of the body fluids (grams) on Day (k).

In a preferred embodiment, after the total amount of the body fluids which was discharged per a first predetermined time period (e.g., six hours or one day) is obtained, the level change of the body fluids discharged in a second predetermined time period (e.g., one menstruation period) which is longer than (or equal to) the first predetermined time period is displayed in the display unit 206 in response to the user's request. Hereinafter, the total amount of the body fluids such as DA or QDA (grams) which was discharged per a predetermined time period is also referred to as "total flow level" or "flow level". For example, after the total flow level of the body fluids which was discharged on each day (at least two days) in the menstruation period is obtained, the level change of the body fluids discharged during the menstruation period is displayed in the display unit 206. Any format which shows a change of level during a period such as a bar chart and a line chart can be used. In a preferred embodiment, a bar chart is used for the display.

Figure 3:
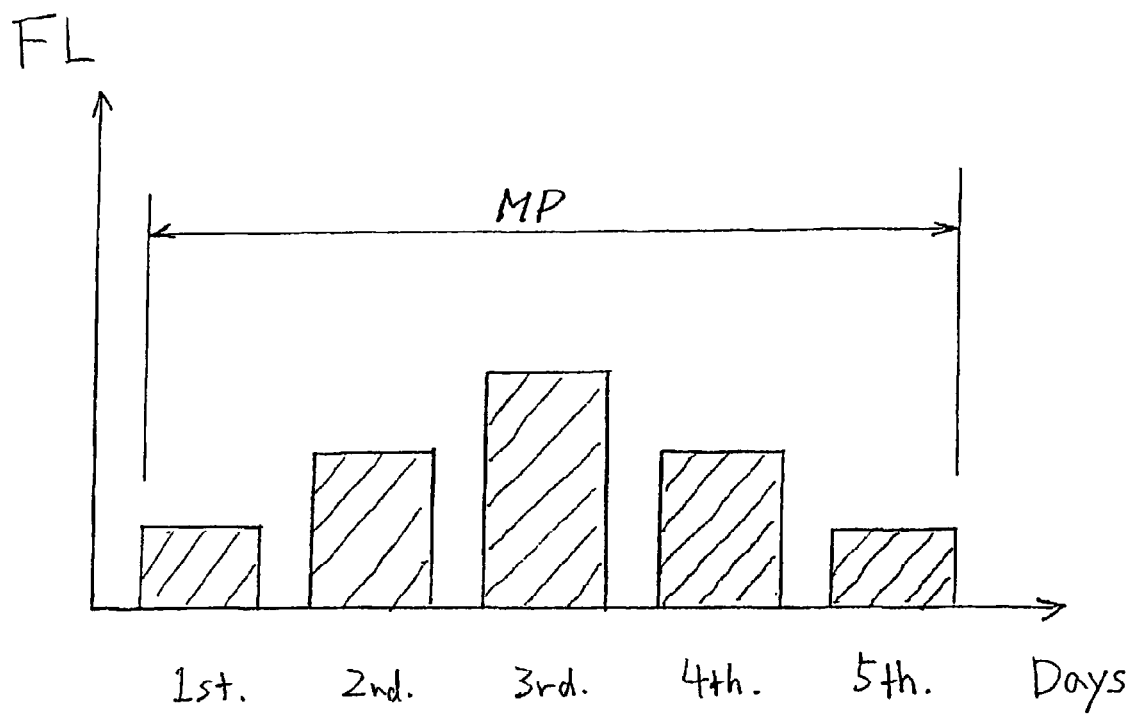
FIG. 3 is an example of a bar chart which shows the flow level change of body fluids discharged during the menstruation period.

FIG. 3 is an example of a bar chart which shows the change of the flow level of body fluids discharged during one menstruation period. In the example of FIG. 3, the horizontal axis shows the days in the menstruation period MP, while the vertical axis shows the flow level FL of body fluids discharged. In this example, the total flow level QDA which was discharged for 6 hours and obtained by the expression (9) is shown as the representative of the flow level discharged in each day of the menstruation period MP. The first predetermined time period is not limited to 6 hours. Any other time period within 24 hours such as 24 hours and 12 hours can be selected as the first predetermined time period.

The level change chart is preferably revised repeatedly when new data or information is inputted by the user and necessary calculation is performed on the new information.

In an alternative embodiment, the flow level change of the body fluids discharged during the menstruation period can be displayed only based on the user's inputs on the total flow level for each day (i.e., without the user's observation and the calculation by the device 200 herein). This is particularly preferred when no observation has made yet and no data or information has been inputted by the user for the body fluids calculation, i.e., at the first time usage of the device 200. Such a level change chart is preferably revised based on the total flow level of the body fluids obtained from above described observation and calculation.

In a preferred embodiment, a disposable absorbent article (i.e., a second disposable absorbent article) to be used by the user is recommended based on the calculation of the flow level of the body fluids, i.e., the total amount of body fluids HA, QDA or DA which was discharged per a predetermined time period (one hour, six hours and 24 hours, respectively). Preferred absorbent articles to be recommended based on QDA are shown in Table III which is described hereinafter.

If a user starts using the device 200 for the first time (thus, no data is available for the previous menstruation cycle), the device 200 requests the user to input an estimated flow level on each day in one typical menstruation period. Each flow level inputted by the user is then converted into pseudo-average amounts of the body fluids discharged per one hour AHA (1), AHA (2), ..., AHA (n) according to Table II which is already described. These pseudo-average amounts of the body fluids are then converted into the amounts of the body fluids discharged per 6 hours QDA (grams) by the mathematical expression (9). The data QDA will be used for the recommendation.

In a more preferred embodiment, once the flow level information is obtained based on the measurement and calculation on the absorbent articles used in the first menstruation period, the trend of flow level change is additionally considered for the recommendation of disposable absorbent articles. The trend of flow level change is indicated by "increasing", "decreasing" or "flat". This trend is determined by the device 200 through the comparison on the data AHA or MHA among two or three (or more if desired) succeeding menstruation periods.

For example, if the trend of flow level is increasing or decreasing on Day (k), the flow level HA (m) on the m-th absorbent article being used and the average flow level AHA (k+1) for the next day are considered for the recommendation. If the trend of future flow level is about flat, the flow level HA (m) on the m-th absorbent article being used and the maximum flow level MHA which were obtained from the previous menstruation period is considered for the recommendation.

The second disposable absorbent article to be recommended is preferably the same type of the first disposable absorbent article which was used for the observation and calculation. For example, the first and second absorbent articles are tampons. Alternatively, the second disposable absorbent article to be recommended can be a different type of the first absorbent article from the one which was used for the observation and calculation. For example, while the first absorbent article is a tampon, the second absorbent article is a sanitary napkin.

If desired, a preferred time period during which the recommended absorbent article is used is also proposed as well as the information about the absorbency type of the absorbent article which should be used in the proposed time period. Preferably, this information is provided through the display unit 206 of the information provider device 200. The preferred time period WT can be obtained by the following mathematical expression:

$$WT = AC/HA \qquad (11)$$

More preferably, information or instruction about the usage of the proposed absorbent article is also provided through the display unit 206 of the information provider device 200.

More preferably, the skill level of using a disposable absorbent article by the user is also considered for the recommendation of disposable absorbent articles. Herein, the term "skill level" of a disposable absorbent article means a measure made by a user's self-judgment about the skillfulness when the article is applied to the user's body. The skill level includes at least two grades (e.g., "skillful" and "not skillful"), preferably at least three grades (e.g., "very skillful", "skillful" and "not skillful" or "first time user"). In the preferred embodiment wherein the disposable absorbent article to be recommended is a tampon product, the skill level assessment having the three grades is preferably applied for the recommendation.

Table III shows an example of recommendation for tampon products based on the flow level and the skill level.

TABLE III

| Skill Level | Flow Level | Recommendation on Tampons Usage |
|---|---|---|
| First Time User | any flow level | Lites |
| Not so Skillful | QDA ≦ 6 grams | Lites |
| Not so Skillful | QDA > 6 grams | Lites or Regular |

TABLE III-continued

| Skill Level | Flow Level | Recommendation on Tampons Usage |
|---|---|---|
| Skillful | QDA ≦ 4 grams | Lites |
| Skillful | 4 < QDA ≦ 6 grams | Lites or Regular |
| Skillful | 6 < QDA ≦ 9 grams | Lites or Regular or Super |
| Skillful | QDA > 9 grams | Lites or Regular or Super or Super Plus |

If desired, two (or more, if further desired) types of disposable absorbent articles are recommended by the information provider device 200. Herein, the term "two types" is intended to mean two disposable absorbent articles which have different absorbencies within the same form of absorbent articles, or which have different forms of absorbent articles. For example, two tampon products which have two different absorbencies such as "Lites" and "Regular" are recommended for one user based on the flow level of body fluids calculated. In another example, one type of tampon product and one type of sanitary napkin product are recommended for one user based on the flow level of body fluids calculated. In these examples, some usage information or instruction about how to use such two types of absorbent articles may be provided through the display unit 206.

(Product Purchase Recommendation)

In a preferred embodiment, the maximum flow level of the body fluids MHA or MQDA (grams) which is discharged in a predetermined time period in the menstruation period is considered for the recommendation of purchasing a disposable absorbent article, i.e. what kinds of absorbency types a user may need to prepare for next menstruation period. Preferred predetermined time periods include, for example, 6 hours, 12 hours, 24 hours (1 day), and 48 hours (2 days). In a preferred embodiment, the maximum flow level of the body fluids MQDA (grams) which is discharged for 6 hours in one day in the menstruation period and obtained by the expression (7) is considered for the recommendation.

Thus, preferred absorbency types of disposable absorbent articles (e.g., tampons) are recommended to the user according to the following Table IV:

TABLE IV

| Flow Level | Recommendation on Tampons |
|---|---|
| MQDA ≦ 4 grams | Lites |
| MQDA ≦ 6 grams | Lites or Regular |
| MQDA ≦ 9 grams | Lites, Regular, or Super |
| MQDA > 9 grams | Lites, Regular, Super, or Super Plus |

In the preferred embodiment wherein the information provider device 200 of the invention is implemented by a network system, information about the consumption of the absorbent products which were recommended and actually used by the user is sent to the server computer from the device 200. The server computer 230 sends an instruction to a seller of disposable absorbent articles to provide the user with disposable absorbent products, based on the information of the consumption.

In a preferred embodiment of the present invention, the information provider device 200 further includes a notification means for notifying the change timing when an absorbent article which is being used is to be replaced with a new one according to the recommended wearing time period calculated by the expression (11). Such an absorbent article being used can be either one which is recommended by the above described manner or one which is chosen by the user without the recommendation by the device 200 (i.e., simply used by the user's judgment). Any notification means known in the art can be used as the notification means. Preferred notification means includes a sound generating means (e.g., an electronic buzzer or alarm), a message indication means (e.g., a liquid crystal display) such as the display unit 206, a light generating means (e.g., a light emission diode (LED)), a vibration generating means, and the like. In a preferred embodiment, the notification means is an electronic buzzer (not shown in FIGS.) which is provided in the information provider device 200 and generates sound in response to a signal sent from the CPU 202.

In this embodiment, the information provider device 200 further includes an input means (e.g., one key in the key board unit 208 or a push button) for inputting timings when the user starts and stop using a disposable absorbent article, and a timer means (not shown in FIGS.) for measuring the lapse of time when the user continues to use the absorbent article. The CPU 202 monitors the lapse of the time through the timer means. When the CPU 202 detects the lapse of time reaches a first predetermined time length which is preliminarily set in the memory unit 204 (only for the first time) or calculated by the expression (11), the CPU 202 generates a signal. The notification means generates a notification signal in response to the signal applied from the CPU 202 so that the user can notice that she or he needs to replace the absorbent article being used with a new one.

In this embodiment, the information provider device 200 further includes a second notification means for alarming the change timing when an absorbent article which is being used needs to be replaced with a new one. According to the second notification, the user is expected to change the absorbent article which is being used immediately. The second predetermined time length which is preliminarily set can be any time length which can be recommended to stop the user's continuous usage of the absorbent article. In the preferred embodiment wherein the disposable absorbent article is a tampon, the second predetermined time length is set at the maximum permissible (or preferred) time length of the tampon for continuous usage, e.g., 8 hours. In an alternative embodiment wherein the disposable absorbent article is a diaper, the predetermined time length is set at the maximum time length of the diaper during which the user can continuously use it with low possibility of leakage, for example, 4 hours. This time length may change depending on the user' urinary load and the diaper design (e.g., the absorbent capacity designed).

Preferably, the information provider device 200 stores, in the memory unit 204, the information about the second predetermined time lengths for disposable absorbent articles. In this embodiment, the user does not set the second predetermined time length by him/her-self since it can be automatically recognized by the CPU 202 when the absorbent article being used is specified. Alternatively, if desired, the user may set the second predetermined time length by him/her-self before starting use of absorbent articles.

In an embodiment wherein a specific absorbent article was recommended by the information provider device 200 and is actually being used by a user, the user does not need to set the predetermined time length. In that embodiment, the CPU 202 automatically recognizes the predetermined time length which is preliminarily stored in the memory unit 204, based on the absorbent article which was recommended and the recommended wearing time period which was calculated by the expression (11).

The notification means preferably includes an indication means such as the display unit 206 which simply shows, in response to the user's request, (a) the change time when an absorbent article which is being used is to be replaced with a new one according to the recommended wearing time period calculated by the expression (11); (b) the recommended wearing time period calculated by the expression (11); (c) the lapse of time after the user started using the current absorbent article which is being used; and/or the remaining time length until the absorbent article which is being used is to be replaced with a new one.

In a preferred embodiment, the information provider device 200 further includes an indication means (e.g., the display unit 206) for indicating a plurality of absorbent products which have different absorbent capacities. Such information or data are preferably stored in the memory unit 204 as well as the corresponding predetermined time lengths on respective articles. The information provider device 200 further includes a selection means (e.g., the keyboard 208) for selecting, among the plurality of absorbent products, one absorbent product which is being used. The notification means notifies the change timing based on the data of the predetermined time length for the specific absorbent product which is being used. Alternatively, the notification means can notify the change timing based on the absorbent capacity of the selected absorbent product if it is possible to predict a preferred time length when the absorbent article is changed based on the absorbent capacity and/or other design factor(s) of the absorbent article.

In a preferred embodiment, the information provider device 200 further includes a means for predicting a date(s) which is important in the menstrual cycle such as the ovulation day, and the starting day of the menstruation period in the next menstrual cycle. In this embodiment, the user is requested by the device 200 to input the dates when the menstruation period starts and ends. The device 200 keeps the data in the memory unit 204 for at least 3 menstrual cycles, preferably more than 10 menstrual cycles. If the CPU 202 detects one menstruation cycle is irregular more than a predetermined time length, e.g., ±5 days compared with the user's average length for one menstruation cycle, the device 200 indicates in the display unit 206 an advice saying "Need to see a doctor since your menstruation cycle is irregular".

Disposable absorbent articles and the information provider device 200 of the present invention may be packaged in a common package as an "education kit". Such an education kit facilitates an appropriate usage especially for a user who has less experience in using disposable absorbent articles (e.g., those who are starting a use of tampon products). Preferably, the packaging associated with such an education kit will include instructions or information about how to use the information provider device 200 and the absorbent articles. Any form of package structures and materials known in the art can be used for the common package.

Alternatively, disposable absorbent articles and the above-described information provider device 200 of the present invention can be distributed to users separately or independently. For example, disposable absorbent articles and the above-described information provider device 200 of the present invention may be marketed independently (i.e., without being packaged within a common package). Alternatively, while disposable absorbent articles are marketed, the information provider device 200 of the present invention may be distributed to users at free. The instructions or information about how to use the information provider device 200 with respects to disposable absorbent articles is preferably attached to the information provider device 200 when it is marketed or distributed.

It is understood that the examples and embodiments described herein are for illustrative purpose only and that various modifications or changes will be suggested to one skilled in the art without departing from the scope of the present invention.

What is claimed is:

1. A device for measuring a body fluid discharged from a body of a user, comprising:
    means for inputting an amount of the body fluid which has been observed to be absorbed by a first absorbent article, the first absorbent article having a predetermined absorbent capacity and being adapted to be disposed adjacent a fluid discharging portion of the body of a user, wherein the amount of the body fluid which has been observed to be absorbed by the first absorbent article is inputted as an area factor input; and
    means for calculating a total amount of the body fluid which was discharged by the user based on the input and the predetermined absorbent capacity of the first absorbent article, wherein the total amount of the body fluid per hour is calculated by $HA = AC \times AF/WT$, wherein HA is flow level of the body fluid in grams/hour, AC is the predetermined absorbent capacity of the absorbent article in grams, AF is the area factor, and WT is wearing time length in hours.

2. The device of claim 1, wherein the first absorbent article is adapted to be disposed adjacent a fluid discharging portion of the body of a user within a first predetermined time period, and the calculation means calculates the total amount of the body fluid discharged within a second predetermined time period.

3. The device of claim 2, wherein the user is a woman, the fluid discharging portion is the vaginal cavity of the woman.

4. The device of claim 1, further comprising means for recommending a second disposable absorbent article.

5. The device of claim 3, wherein the first absorbent article is a tampon, an interlabial product, or a sanitary napkin.

6. A method for measuring an amount of body fluid discharged from a body of a user, comprising the steps of:
    (a) providing a device for measuring a body fluid discharged from a body of a user, said device comprising:
        means for inputting an amount of the body fluid which has been observed to be absorbed by a first absorbent article, the first absorbent article having a predetermined absorbent capacity and being adapted to be disposed adjacent a fluid discharging portion of the body of a user, wherein the amount of the body fluid which has been observed to be absorbed by the first absorbent article is inputted as an area factor input; and
        means for calculating a total amount of the body fluid which was discharged by the user based on the input and the predetermined absorbent capacity of the first absorbent article, wherein the total amount of the body fluid per hour is calculated by $HA = (AC \times AF + LF)/WT$, wherein HA is flow level of the body fluid in grams/hour, AC is the predetermined absorbent capacity of the absorbent article in grams, AF is the area factor, LF is the leakage factor, and WT is wearing time length in hours;
    (b) putting a disposable first absorbent article having a predetermined absorbent capacity to a fluid discharging portion of the user;

(c) observing an amount of the body fluid which is absorbed by the absorbent article, wherein the amount of the body fluid which has been observed to be absorbed by the first absorbent article is inputted into said device through the means for inputting as an area factor input;

(d) observing a degree of leakage, wherein the degree of leakage which has been observed is inputted into said device through the means for inputting as a leakage factor; and (e) calculating through said means for calculating the total amount of the body fluid which was discharged by the user based on the observation of step (c), the observation of step (d), and the predetermined absorbent capacity of the first absorbent article, wherein the total amount of the body fluid per hour is calculated by HA=(AC×AF+LF)/WT, wherein HA is flow level of the body fluid in grams/hour, AC is the predetermined absorbent capacity of the absorbent article in grams, AF is the area factor, LF is the leakage factor, and WT is wearing time length in hours.

7. The method of claim 6, further comprising the steps of:

(f) repeating steps (b), (c), (d) and (e) using a second disposable absorbent article for a first predetermined time period thereby calculating the total amount of the body fluid discharged for a second predetermined time period by the step (d).

8. A device for showing a flow level trend of a body fluid discharged from a body of a user, comprising:

means for inputting an amount of the body fluid which has been observed to be absorbed by a first absorbent article over a first predetermined time period, the first absorbent article having a predetermined absorbent capacity and being adapted to be disposed adjacent a fluid discharging portion of the body of a user, wherein the amount of the body fluid which has been observed to be absorbed by the first absorbent article over said first predetermined time period is inputted as an area factor input;

means for calculating the flow level of said body fluid which was discharged by the user based on said input and said predetermined absorbent capacity of said first absorbent article, wherein the flow level is calculated by HA=AC×AF/WT, wherein HA is flow level of the body fluid in grams/hour, AC is the predetermined absorbent capacity of the absorbent article in grams, AF is the area factor, and WT is wearing time length in hours; and means for displaying the trend of the discharged body fluid flow level over a second predetermined time period.

9. The device of claim 8, wherein the trend of the discharged body fluid flow level is shown in a bar chart.

10. A method for showing, in a display, a flow level trend of a body fluid discharged from a body of a user, comprising the steps of:

providing a device for measuring a flow level of a body fluid discharged from a body of a user, said device comprising:

means for inputting an amount of the body fluid which has been observed to be absorbed by a first absorbent article, the first absorbent article having a predetermined absorbent capacity and being adapted to be disposed adjacent a fluid discharging portion of the body of a user, wherein the amount of the body fluid which has been observed to be absorbed by the first absorbent article is inputted as an area factor input; and means for calculating the flow level change of the body fluid which was discharged by the user based on the input and the predetermined absorbent capacity of the first absorbent article, wherein the flow level change is calculated by HA=AC×AF/WT, wherein HA is flow level of the body fluid in grams/hour, AC is the predetermined absorbent capacity of the absorbent article in grams, AF is the area factor, and WT is wearing time length in hours;

measuring a flow level of a body fluid discharged from a body over a first predetermined time period using said device, wherein the amount of the body fluid which has been observed to be absorbed by said first absorbent article having a predetermined absorbent capacity is inputted as an area factor input, and wherein the flow level of the body fluid is calculated by HA=AC×AF/WT, wherein HA is flow level of the body fluid in grams/hour, AC is the predetermined absorbent capacity of the absorbent article in grams, AF is the area factor, and WT is wearing time length in hours; and displaying the flow level trend of the discharged body fluid level in the display over a second predetermined time period.

* * * * *